(12) United States Patent
Olguin

(10) Patent No.: US 6,365,199 B1
(45) Date of Patent: Apr. 2, 2002

(54) HAIR GROWTH STIMULANT

(76) Inventor: Marsha E. Olguin, 1065 W. Lomita Blvd., Space 396, Harbor City, CA (US) 90710

(*) Notice: Subject to any disclaimer, the term of this patent is extended or adjusted under 35 U.S.C. 154(b) by 0 days.

(21) Appl. No.: 09/636,414

(22) Filed: Aug. 10, 2000

Related U.S. Application Data

(62) Division of application No. 09/179,732, filed on Oct. 27, 1998, now Pat. No. 6,159,475.
(60) Provisional application No. 60/064,377, filed on Nov. 6, 1997.

(51) Int. Cl.[7] .................. A61K 31/205; A61K 31/35; A61K 31/352; A61K 31/495; A61K 7/06; A61K 31/047; A61K 31/05; A61K 31/14; A61K 31/191; A61K 31/4406; A61K 33/32; A61K 35/78

(52) U.S. Cl. .................. 424/736; 424/602; 424/639; 424/724; 424/731; 424/DIG. 6; 514/249; 514/356; 514/451; 514/453; 514/456; 514/457; 514/458; 514/464; 514/474; 514/547; 514/552; 514/554; 514/556; 514/558; 514/560; 514/574; 514/642; 514/729; 514/783; 514/880; 514/881

(58) Field of Search .................. 424/736, 602, 424/639, 724, 731, DIG. 6; 514/547, 552, 783, 880, 881, 249, 356, 451, 453, 456–458, 464, 474, 558, 560, 554, 556, 574, 642, 729

(56) References Cited

PUBLICATIONS

Chemical Abstracts 76:144805, abstracting ZA 7002048, May 1971.*
Derwent Abstract 1987–084841, abstracting SU 1247011, Jul. 1986.*

* cited by examiner

*Primary Examiner*—John Pak
(74) *Attorney, Agent, or Firm*—Beehler & Pavitt; Norton Townsley

(57) ABSTRACT

A hair growth formulation. The two basic main ingredients are castor oil and a special lemon extract. The special lemon extract is made from fresh lemon peel. The peel, including the bioflavonoids membrane, is blended with purified water until it is liquidified. Then the mixture is filtered through a sanitized cloth. Other ingredients that have been found helpful include: inositol, choline (from bitartate), niacinamide or nicotinic acid, manganese in chelated form, bioflavonoids, and folic acid. Finally perfume and sodium benzoate (as a preservative) can be added.

6 Claims, No Drawings

HAIR GROWTH STIMULANT

REFERENCES

This application is a divisional of Ser. No. 09/179,732, filed on Oct. 27, 1998, which is now U.S. Pat. No. 6,159,475, which claims the benefit of U.S. provisional patent application No. 60/064,377 filed Nov. 6, 1997.

BACKGROUND OF THE INVENTION

The present invention relates to the field of scalp stimulation and in particular to the field of hair growth stimulants.

There are many products on the market that claim to grow hair. Most do not. Products on the market that can actually grow hair are expensive and available only by prescription. Furthermore, cessation of use usually results in immediate hair loss. In other words, once a user starts using this prescription product, he or she must continue for life in order to maintain hair.

In the past it was believed that, once the hair root would not produce a follicle, the root was dead and could not be restored. But little research has been done for periods of seven and up to eleven years after the hair root has failed to produced a shaft. Results produced with this invention have proved that there is a window of time in which one can, in fact, regenerate or revive the hair root.

Development of a simple, inexpensive treatment which can grow hair represents a great improvement in the field of scalp stimulation and satisfies a long felt need of bald persons, balding persons, persons with thin or sparse hair, and their doctors and cosmeticians.

SUMMARY OF THE INVENTION

The present invention is a unique lotion or cream formula that can regenerate some follicles which are still alive but in a state of non productivity (the resting phase). There is no product now on the market which will enhance the growth of eyebrows and beards. Yet, this product can stimulate the growth of some eyebrow tips, as long as the roots are in this resting stage, can enlarge mustaches or enhance the fullness of the mustache, and can enhance beards that have been growing sparely.

People are balding for many reasons but the majority have nutritional deficiencies. This formula has regenerated hair growth even for people that have been bald for over ten years but not longer than fourteen years. It has strengthened hair for people as elderly as 94. What makes this product unique are the natural ingredients that produce it. It is made from the oil of a lemon and minerals. The acidity of the lemon along with choline, inositol and niacinamide or nicotinic acid stimulate the follicle while it is in the inactive stage. This product is revolutionary in that it is totally a natural product, except for the preservative and fragrance.

The main active ingredients of this invention are castor oil and a special lemon extract. The extract is made by blending fresh lemon peel with purified water and filtering the product through a sanitized cloth. The ratio is approximately 10–600 cc castor oil and approximately 5–340 cc special lemon extract. Other ingredients that can be beneficially added to the formulation are: inositol, choline from bitartrate, niacinamide or nicotinic acid, manganese in chelated form, bioflavonoids, and folic acid. Some perfume and a preservative may also be added.

An appreciation of the other aims and objectives of the present invention and an understanding of it may be achieved by referring to the following description of a preferred embodiment.

DETAILED DESCRIPTION OF THE PREFERRED EMBODIMENT

This product has regenerated a larger percent than any among the topical products. The highest success rate is with people with receding hairlines. This invention has regenerated hair that has been absent for over eleven years on people of all ages from age 16 to 94. Minimal use of the product, even as little as once a week has regenerated hair. Some hair follicles can be revived and stimulated by concentrated amounts of certain vitamins and, minerals not present in the tissue at the base of the follicle. Vitamins and minerals revive the hair bulb and nourish it with the proper amounts needed to stimulate the root into action.

Heredity, stress and poor diet prevent normal cycles of hair growth. Not all hair bulbs can be stimulated into performance, but there are many people who can be helped by application of the following formula:

| | |
|---|---|
| 10–500 cc | Castor Oil |
| 5–340 cc | Special Lemon Extract |
| 50–1900 cc | Inositol |
| 50–1900 cc | Choline bitartrate |
| 250–2500 cc | Niacinamide[1] or nicotinic acid |
| 40–300 IU | Manganese in chelated form |
| 4–1900 IU | Bioflavonoids[2] |
| 40–500 IU | Folic Acid[3] |
| 5 Drops | Perfume Oil |
| | Sodium benzoate (as a preservative) |

[1]Containing Niacinamide, Dicalcium Phosphate, Cellulose, Stearic Acid, Magnesium Stearate and Silica.
[2]Containing: Flavanones 350 mg, Hesperidins 154 mg, Naringen & Naringenin 14 mg, Eriocitrin 112 mg, Flavonols 308 mg, Flavones 42, Rutin 100 mg.
[3]Containing Dibasic Calcium Phosphate, Crosscarmellose Sodium, Magnesium Stearate, Folic Acid.

The powdered ingredients are sifted twice to minimize granules present. Then fresh lemon peel of one lemon, of the Rutaceae family, is scrubbed with a brush and cut up into ¼ inch pieces, including the bioflavonoids membrane, then put in a blender with three to four ounces of purified water until it is liquidified. Then the mixture is filtered through a press. The press consists of a sanitized cloth, to filter out the precious liquid. This lemon fluid is somewhat thick in substance and is measured. This essence is the main active ingredient of the formula. This fluid is both lemon oil and bioflavonoid from the membrane around the peel. The bioflavonoids boost the acidity in the lemon rind, acting as an activator for the lethargic follicle. The acidity in combination with the choline, inositol and niacinamide or nicotinic acid stimulates the follicle into production. The choline is important for development of the cell membrane. Inositol is essential for the growth of human cells but only myo-inositol is of importance here.

Castor oil, a prepared oil from the plant ricinus communis of the Euphorbiaceae family contains many glycerides of which linoleic acid is one. A deficiency of linoleic acid has caused severe hair loss in canines, according to experiments. The same seems to be true Oman. The niacinamide or nicotinic acid opens up the blood vessels to accept nourishment into the hair root and the follicle is stimulated out of its resting state. Folic acid, in conjunction with this formula, causes adequate oxygenation of the blood supplying the scalp or other treated area. Inositol, works to metabolize amino and fatty acids in the skin. The blood vessels in turn nourish the root and stimulating rapid growth. The average growth of one hair is ¼ of an inch a month. After being treated with this formula, hair has grown 1/8 of an inch in two weeks on some clients.

The two basic main ingredients that will grow hair are castor oil and lemon extract. It has been found that the formulation will work with castor oil and lemon extract in any of the following ratios:

| Castor oil | 10 cc | 10 cc | 240 cc | 480 cc | 600 cc | 100 cc |
|---|---|---|---|---|---|---|
| Lemon extract | 5 cc | 25 cc | 180 cc | 255 cc | 340 cc | 75 cc |

The formulation will grow hair if the ratio of castor oil to lemon extract is anywhere from 0.4 to 1 to 2 to 1.

This product can help those individuals with baldness arising from these three conditions. It has also helped those prone to baldness at an early age.

EXAMPLES

One client had three completely bald sections on her head for eleven years. She used the hair growth formula described above only three times a week. After seven months the right and left sides of her head had completely filled and the top was slowly filling also.

Another client using the formulation had 50 new hairs grow in a 2 square inch radius. This client had been bald for over ten years.

Yet another client using the formulation, who has thinning hair, has grown 38 new hairs in a 2-inch square section.

The hair growth formula has been described with reference to a particular embodiment. Other modifications and enhancements can be made without departing from the spirit and scope of the claims that follow.

What is claimed is:

1. A hair growth formula comprising:
   a. 10–600 cc castor oil;
   b. 5–340 cc special lemon extract; said special lemon extract comprising fresh lemon peel made into a puree by blending with purified water until liquified and said puree being filtered through a sanitized cloth;
   c. 50–1900 cc inositol;
   d. 50–1900 cc choline bitartrate;
   e. 250–2500 cc of a chemical selected from the group consisting of niacinamide with dicalcium phosphate, cellulose, stearic acid, magnesium sterate and silica, and nicotinic acid;
   f. 40–300 IU manganese in chelated form;
   g. 4–1900 IU bioflavonoids, containing: flavanones, hesperidins, naringen and naringenin, eriocitrin, flavonols, flavones, and rutin;
   h. 40–500 IU folic acid, with dibasic calcium phosphate, crosscarmellose, sodium, and magnesium stearate;
   i. 5 drops perfume oil; and
   sodium benzoate.

2. A hair growth formula as claimed in claim 1 in which the ratio of said lemon peel to said purified water is the peel of one lemon to three to four ounces of purified water.

3. A hair growth formula as claimed in claim 1 in which the ratio of castor oil to special lemon extract is from about 0.4 to 1 to about 2 to 1 by volume.

4. A method of mixing a hair growth formula comprising:
   a. providing castor oil, inositol, perfume oil, a sanitized filter cloth, purified water and sodium benzoate;
   b. providing choline bitartrate;
   c. providing niacinamide containing dicalcium phosphate, cellulose, stearic acid, magnesium stearate and silica;
   d. providing nicotinic acid;
   e. providing manganese in chelated form;
   f. providing bioflavonoids, containing flavanones, hesperidins, naringen and naringenin, eriocitrin, flavonols, flavones, and rutin;
   g. providing folic acid with dibasic calcium phosphate, crosscarmellose, sodium, and magnesium stearate;
   h. providing fresh lemon peel;
   i. scrubbing said fresh lemon peel with a brush;
   j. cutting up said fresh lemon peel into 1/4 inch pieces;
   k. blending said fresh lemon peel in a blender with said purified water until it is liquified
   l. filtering said blended lemon peel through said sanitized cloth to produce a special lemon extract;
   m. sifting said inositol, sodium bezoate, choline, niacinamide, nicotinic acid, manganese, bioflavonoids, and folic acid;
   n. mixing 5–340 cc of said special lemon extract, 10–600 cc of said castor oil, 50–1900 cc of said inositol, 50–1900 cc of said choline, 250–2500 cc of a chemical selected from the group consisting of said niacinamide and said nicotinic acid, 40–300 IU of said manganese, 4–1900 IU of said bioflavonoids, 40–500 IU of said folic acid, 5 drops of said perfume oil; and sodium benzoate.

5. A method as claimed in claim 4 in which the ratio of said lemon peel to said purified water is the peel of one lemon to three to four ounces of purified water.

6. A method as claimed in claim 4 in which the ratio of castor oil to special lemon extract is from about 0.4 to 1 to about 2 to 1 by volume.

* * * * *